(12) United States Patent
De Gruytere

(10) Patent No.: US 10,786,385 B2
(45) Date of Patent: Sep. 29, 2020

(54) PROFILE FOR THE ATTACHMENT OF AN IMMOBILISATION MASK

(71) Applicant: ORFIT INDUSTRIES, Wijnegem (BE)

(72) Inventor: Simon De Gruytere, Meerhout (BE)

(73) Assignee: ORFIT INDUSTRIES, Wijnegem (BE)

( * ) Notice: Subject to any disclaimer, the term of this patent is extended or adjusted under 35 U.S.C. 154(b) by 531 days.

(21) Appl. No.: 15/515,860

(22) PCT Filed: Sep. 30, 2014

(86) PCT No.: PCT/EP2014/070880
§ 371 (c)(1),
(2) Date: Mar. 30, 2017

(87) PCT Pub. No.: WO2016/050275
PCT Pub. Date: Apr. 7, 2016

(65) Prior Publication Data
US 2017/0252201 A1    Sep. 7, 2017

(51) Int. Cl.
*A61B 6/04* (2006.01)
*A61F 5/37* (2006.01)
*A61B 90/18* (2016.01)
*A61N 5/10* (2006.01)

(52) U.S. Cl.
CPC .......... *A61F 5/3769* (2013.01); *A61B 6/0428* (2013.01); *A61B 90/18* (2016.02); *A61F 5/3707* (2013.01); *A61N 5/1077* (2013.01); *A61N 2005/1087* (2013.01); *A61N 2005/1097* (2013.01)

(58) Field of Classification Search
CPC ....... A61B 90/18; A61B 6/037; A61B 6/0428; A61B 6/0421; A61F 5/3707; A61F 5/3776; A61F 5/3723; A61F 5/3769; A61G 13/121; A61G 13/1235; A61G 13/1245; A47C 15/008; A61N 2005/1097
See application file for complete search history.

(56) References Cited

U.S. PATENT DOCUMENTS 5,848,449 A * 12/1998 Hauger ................ A61B 6/0421
5/637
2015/0053213 A1* 2/2015 Nieberding .......... A61B 6/0428
128/869

FOREIGN PATENT DOCUMENTS

| CN | 203102883 U | 7/2013 |
| CN | 203562724 U | 4/2014 |
| EP | 1095640 A1 | 5/2001 |
| EP | 2583634 A1 * | 4/2013 ............. A61B 90/18 |

(Continued)

*Primary Examiner* — Ophelia A Hawthorne
(74) *Attorney, Agent, or Firm* — Browdy and Neimark, PLLC

(57) ABSTRACT

An assembly of a carrier for supporting a patient, an immobilization mask and connection means for connecting the carrier with the immobilization mask, wherein the connection assembly contains a profile that is provided on a first side to be connected to the immobilization mask and on a second side contains a first connector for connecting the immobilization mask to the carrier, the connection assembly including a carrier connector disposed on the carrier, the first connector being provided to engage the corresponding carrier connector, wherein a swivel and a swivel anchor point are provided to cooperate such that when swivelling the swivel arm around the swivel anchor point towards the carrier, the first connector is guided to a connected state.

20 Claims, 5 Drawing Sheets

(56) References Cited

FOREIGN PATENT DOCUMENTS

| EP | 2583634 A1 | 4/2013 |
|----|------------|--------|
| WO | 2014091407 A1 | 6/2014 |

* cited by examiner

PROFILE FOR THE ATTACHMENT OF AN IMMOBILISATION MASK

FIELD

This invention concerns an assembly of a carrier for supporting a patient and an immobilisation mask that is connectable to the carrier for immobilizing a body part of the patient on the carrier, the carrier and the immobilization mask containing cooperating connection means.

This invention also concerns an immobilization mask for immobilizing a body part of a patient on a carrier, the immobilization mask containing a sheet of a thermoplastic material for receiving the body part to be immobilized, and connection means for connecting the immobilization mask to the carrier.

This invention further concerns a profile for connecting an immobilization mask for immobilizing a body part of a patient on a carrier, to the carrier.

BACKGROUND

The use of masks or similar means for positioning one or more body parts of a patient in a predetermined position on the carrier and immobilizing of the body part in this position in a predetermined posture during the treatment of the patient with radiation, such as for example with Intensity Modulated Radiation Therapy (IMRT), Image Guided Radiation Therapy (IGRT), stereotactic radiation therapy or surgery and proton therapy, is well known. With such techniques, the accurate and reproducible positioning of the body part to be treated of a predetermined position in a predetermined posture is of utmost importance. As use is often made of a radiation source that has the shape and/or size of the tissue to be treated, it is therefore essential that the radiation is directed at the tumour, and to spare the surrounding healthy tissue. Deviations of a few mm may result in that not the tumour is irradiated, but the surrounding healthy tissue, which is thus destroyed or damaged. This is undesirable.

Treatment and imaging techniques that make use of charged, heavy particles such as protons, offer the advantage in comparison to other radiation sources such as electrons, photons, gamma or X-radiation that the radiation dose can be better directed to the tissue to be treated. Proton beams usually scatter less in the tissue to be treated and exhibit a low lateral dispersion, which limits the risk of lateral damage. This offers the advantage that a directed killing of tumour cells can be obtained and that the surrounding healthy tissue can be spared. In order to enable the directed killing of unwanted tissue with both more or less dispersing radiation beams, an accurate positioning of the body part to be treated in relation to the radiation source is essential. To minimize the risk of unwanted irradiation of surrounding tissue, it is not only required that the body part is accurately positioned in the desired posture in relation to the radiation source during the treatment, but also that the body part is fixated during the treatment in the intended posture and that the range of motion during the treatment is limited to a minimum. An accurate and reproducible positioning is of importance during fractionated treatment in which the patient is administered repeated radiation doses of less than optimal dose with in-between time intervals, to ensure sufficient radiation of the area to be treated and to limit the irradiation of healthy tissue to a minimum. An accurate positioning is also exceptionally important during a single treatment, in which a large radiation dose is administered once. Various tools have been designed to realize an accurate and reproducible positioning of a body part in relation to a radiation source, both with regard to the position as well as the posture, and thereby also to limit the range of motion of the body part to a minimum.

Traditionally, a patient is placed on a table, on which a base plate or carrier is located. Base plates that are used with radio therapy are often manufactured as a sandwich structure with a foam core and carbon fibre skin. Immobilizing a body part of a patient, such as for example the head or any other body part, on a particular place on the table in a predetermined posture is realized by attaching an immobilization mask to the base plate or the table. The immobilization mask has a shape that closely matches the body part to be immobilized, to limit the range of motion of the body part to be immobilized.

WO2014/091407 A1 in the name of the applicant discloses such a non invasive immobilization mask comprising a sheet of thermoplastic material for immobilizing the head of a patient in a predetermined position on a base plate or carrier, in a predetermined posture. The mask comprises a sheet of a thermoplastic material which is formed such that it matches the shape of the body part to be immobilized. To enable optimum design, a thermoplastic material is chosen with a low melting temperature, such that the material can be shaped directly onto the body part. An example of a suitable material is ε-polycaprolactone. Means are provided to at least a section of the edge of the sheet of thermoplastic material for attaching the mask to the base plate. The attachment means disclosed in WO2014/091407 A1 comprise a first lower lip for the attachment of the immobilization mask to the outer edge of a base plate or carrier.

To meet the special requirements set by the radiation therapy concerning the immobilization of the patient in relation to the radiation source and, especially with proton therapy, homogeneity of the radiation that reaches the tissue to be treated, the carrier is designed such that it supports the patient well.

The immobilization mask according to WO2014/091407 may however be quite cumbersome to secure to the carrier. The person applying the mask usually stands at the head of the patient, looking down onto the patient, and would for example firstly connect a first profile at the top of the patient's head to the carrier. He would then connect the two profiles on the left and right sides of the mask to the carrier on the respective sides of the head. As the dimensions of the carrier at the location of the head are often smaller than the dimensions of the head, in order to avoid scattering and alteration of the radiation beam emitted to the patient by the radiation source, the connecting means will often be positioned behind the head of the patient in the connected state, and the visibility for the person fixing the mask will thus be bad as that person looks down onto the patient. Consequently, it may take too much time to find the right position of the connecting means on the carrier, as it may take several attempts to find the correct position of the connection means in the connected state. This may cause discomfort and stress to the patient.

Consequently, there is a need for attachment means for attaching an immobilization mask to a carrier or base plate for the support of the patient that allows connecting the profile to the carrier more quickly.

SUMMARY

This is achieved according to the invention with an assembly for radiation therapy, for example proton therapy, of a carrier for supporting a patient, an immobilization mask connectable with the carrier for immobilizing a body part of the patient onto the carrier and connection means for connecting the carrier with the immobilization mask, wherein the immobilization mask contains a sheet of a thermoplastic material for receiving the body part to be immobilized, wherein the connection means contain at least one profile that is provided on a first side to be connected to the immobilization mask and on a second side opposite the first, contains first connection means for connecting the immobilization mask to the carrier, the connection means comprising carrier connection means on the carrier, the first connection means being provided, in the connected state, to engage the corresponding carrier connection means, wherein the profile comprises at least one swivel arm, in that the carrier comprises a swivel anchor point and the swivel and the swivel anchor point are provided to cooperate such that when swivelling the swivel arm around the swivel anchor point towards the carrier, the first connection means are guided to the connected state where they engage the corresponding connection means.

To this end, the assembly of this invention is characterized in that the profile comprises at least one swivel arm, in that the carrier comprises a swivel anchor point and in that the swivel and the swivel anchor point are provided to cooperate such that when swivelling the swivel arm around the swivel anchor point towards the carrier, the first connection means are guided to the connected state where they engage the corresponding carrier connection means.

It has been found that connecting the swivel arm to the swivel anchor point is easier to obtain for a person than directly positioning the first connection means to the connected state as it has been found that connecting the swivel arm and the swivel anchor point to each other is relatively easy to be performed. When having connected the swivel arm and the swivel anchor point, the person can then bring the first connection means to the connected state by simply swivelling the swivelling arm around the anchor point. As the swivelling can be performed without needing a clear view on the swivelling, positioning the first connection means into the connected state can be performed more easily, even when the connected state of the first connection means is hidden behind the head of the patient for the person connecting the profile to the carrier.

To ensure that mainly the tissue to be treated is irradiated and the risk of undesired irradiation of surrounding tissue is kept to a minimum, it is of importance that the body part to be immobilized is fixated during the treatment at the intended place and in the intended posture and that the range of motion during the treatment is limited to a minimum. Therefore, it is of importance that the immobilization mask closely fits the body part to be immobilized, which implies that the material of the mask, but also the profile, in the connected state with the carrier, are subjected to great tensile force and stress. The connection means or the profile of this invention enable, despite a high tensile force on the profile, to establish and maintain a connection.

The profile preferably engages in the thickness direction onto the carrier, this is usually the direction wherein the tensile force and tension onto the immobilization mask and profile are the greatest. Since the profile engages in the thickness direction, optimal transfer of forces from the mask to the carrier is accomplished.

According to preferred embodiments of the present invention, the connection means contain at least one profile that is provided on a first side with second connection means to be connected to the immobilization mask, more in particular to the sheet of the mask.

According to preferred embodiments of the current invention, the first connection means comprise a first lip that is provided, in the connected state, to extend along the carrier.

The profile preferably contains a first lower lip which is provided, in the connected state, to extend along a lower surface of the carrier, wherein the edge of the carrier is held between said upper and lower lip. In a further preferred embodiment, this lip is resiliently arranged to facilitate the establishment and severing of the connection. To promote an accurate and reproducible positioning of the profile onto the carrier, on a lower surface of the carrier, a guide is preferably provided for guiding the displacement of the lower lip to the position where the lip engages the carrier, at the connection of the immobilization mask to the carrier.

According to preferred embodiments of the present invention, the swivel arm and the swivel anchor point engage each other. It has been found that such engagement allows a connection of the swivel arm and the swivel anchor allowing the swivelling motion without increasing the risk that the swivel anchor point and the swivel arm unwantedly release each other during swivelling.

According to preferred embodiments of the present invention, the engagement of the swivel arm and the swivel anchor point has substantially a single degree of freedom, preferably the angle of rotation of the swivel arm around the swivel anchor point during swivelling of the swivel arm. It has been found that such engagement further facilitates the bringing of the first connection means into the connected position.

According to further preferred embodiments of the present invention, the swivel arm comprises a gripping part provided to grip at least partly around the swivel anchor point. It has been found that such a swivel arm can be relatively easily made and is relatively easy to apply around the swivel anchor point even should the swivel anchor point be occluded by the patient.

According to further preferred embodiments of the present invention, the swivel anchor point comprises a cylindrical protrusion provided to be surrounded at least partly by the gripping part when it grips at least partly around the swivel anchor point. It has been found that such cylindrical protrusion allows to be relatively easily produced on the carrier. Moreover, it has been found that such protrusion is relatively easy to locate, for example by touch should the swivel anchor point be occluded by the patient.

According to embodiments of the present invention, the swivel arm and the swivel anchor point are connected to each other in a hinge joint. It has been found that such connection is relatively easily to be created whereas limiting the number of degrees of freedom to one.

According to preferred embodiments of the current invention, the swivel arm extends along the first connection means. Such embodiment has been found the increase the strength with which the mask can be attached to the carrier as the length of the first connection means can be increased along the swivel arm.

According to preferred embodiments of the current invention, wherein the swivel arm extends along the second connection means. Such embodiment has been found to increase the strength with which the mask, more in particular the sheet of thermoplastic material, can be attached to the profile as the length of the second connection means can be increased along the swivel arm.

According to preferred embodiments of the current invention, the swivel anchor point is visible for the person applying the immobilization mask to the patient while the patient is positioned on the carrier such as to further allow the ease with which the immobilization mask is connected to the carrier.

According to preferred embodiments of the current invention, the body part is a head and the swivel anchor point is provided below the mandible of a patient positioned on the carrier. Such an embodiment has been found to further increase the strength with which the head of the patient is immobilized to the carrier.

According to preferred embodiments of the current invention, the corresponding carrier connection means are positioned along the outer edge of the carrier. A profile that engages an outer edge of the carrier is simple to attach, also if a tensile force must be exerted onto the profile and/or the mask with which the profile is connected, to establish the connection. With a profile that engages the outer edge of the carrier, such a force is easier to exert then with the use of relatively small pins, which detach relatively easy when subjected to a large tensile force.

According to preferred embodiments of the current invention, the swivel anchor point is provided below the mental protuberance of the mandible of the patient as it has been found that such a positioning of the swivel anchor point further increases the stability of the immobilization of the head of the patient positioned on the carrier, especially when the swivel arm extends along the second connection means as in such an embodiment the sheet of thermoplastic material can extend along the swivel arm and thus can also extend over the full chin of the patient when applied over the mental protuberance such that a further stabilization of the immobilization can be obtained.

According to more preferred embodiments of the current invention, the swivel anchor point is provided at the height of laryngeal prominence, also called Adam's apple, of the patient.

According to preferred embodiments of the current invention, the body part is a head and the swivel anchor point is located along the neck of a patient positioned on the carrier. The swivel anchor point located in such a position has been found to allow an improved immobilization of the patient on the carrier without unduly increasing the amount of scattering caused by the presence of the additional material of the swivel arm and the sheet of thermoplastic material.

According to more preferred embodiments of the current invention, the swivel anchor point is located along the neck of a patient positioned on the carrier above the clavicle of the patient as in such position a good balance has been found between immobilization of the head of the patient and scattering of the radiation due to the presence of the profile and the sheet of thermoplastic material.

According to preferred embodiments of the current invention, the sheet of thermoplastic material is covered with an antibacterial coating as such coating decreases the risk of contamination of the patient positioned on the carrier. The aim of this invention consists as well in providing an immobilization mask that is provided with connection means for connecting the mask to the carrier, wherein the connection means exhibit an improved mechanical strength and longer operating life, while also making the fixation of the mask on the patient's head more practicable for the practitioner and more comfortable for the patient.

The immobilization mask according to the invention and preferred embodiments thereof are disclosed in the attached claims, figures and figure description.

The aim of this invention consists further in connection means, in particular in providing a profile for attaching an immobilization mask to a carrier for supporting a patient, wherein the connection means exhibit improved mechanical strength and a longer operating life as well as making the fixation of the mask on the patient's head more practicable for the practitioner and more comfortable for the patient.

BRIEF DESCRIPTION OF THE DRAWINGS

The profile according to the invention and preferred embodiments thereof are disclosed in the attached claims, figures and figure description.

The invention is illustrated in the accompanying drawings which display preferred embodiments and describe the profile, the immobilization mask provided with a profile, and an assembly of a carrier, an immobilization mask and profile for the connection of the immobilization mask to the carrier or base plate or carrier on which the patient rests. The invention is further illustrated in the description of the figures of these preferred embodiments. In the following figure description, the same reference numbers refer to the same elements.

FIG. 7b shows a cross-section of FIG. 7a. FIG. 7c shows a view of the carrier used in FIG. 7a.

DETAILED DESCRIPTION

Figure 7A:
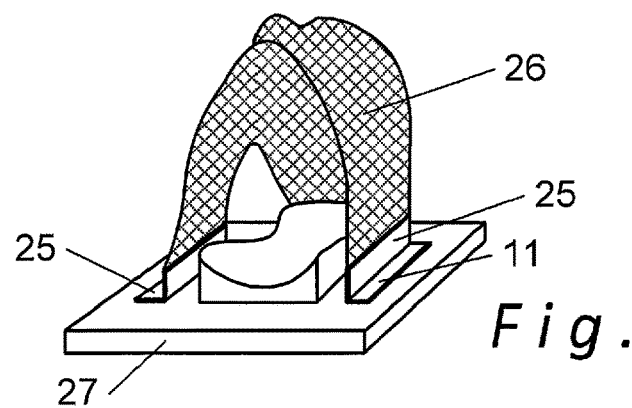
FIG. 7a shows a view to the immobilization mask connected with a carrier according to the state of the art.
Figure 7B:
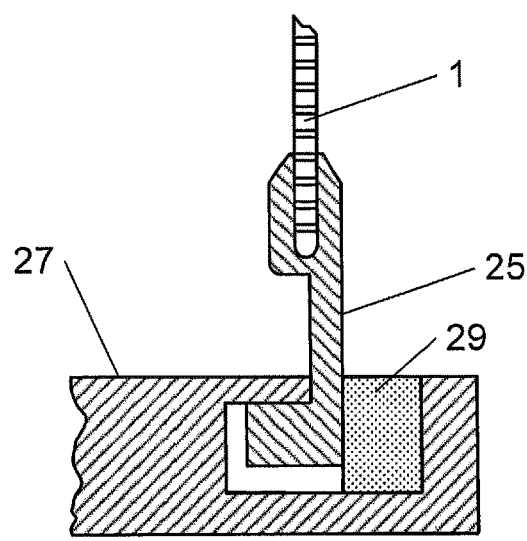
Figure 7C:
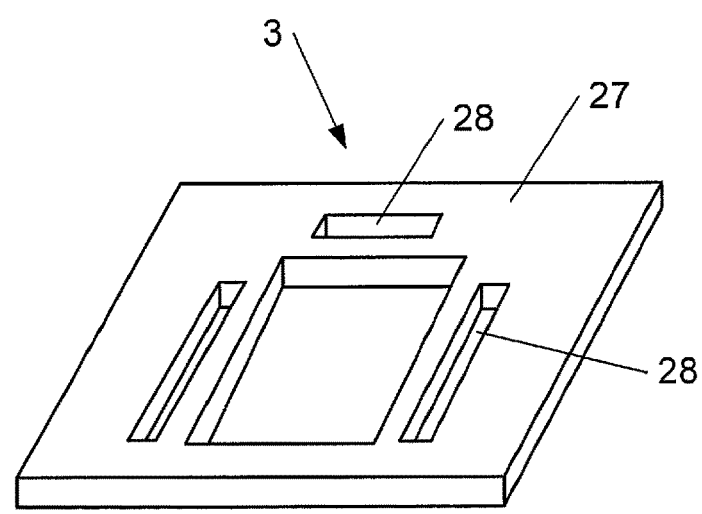

FIGS. 7a, 7b and 7c show the way in which in the state of the art a connection was established between a mask 26 for immobilizing a body part of a patient, for example the head, and a carrier 27 on which the patient rests. As is shown in FIG. 7a, it is known from the state of the art to provide an L-shaped profile 25 along the edge of the mask that engages an opening or slot 28, provided in the surface of the carrier, in the region of the position where the patient rests. The slot 28 needs to be relatively wide, to enable the displacement of the L-shaped profile through the slit to enable its application. To fixate the position of the profile into the slot and to prevent displacement, it is necessary to apply a positioning block 29 or the like into the slot. The presence of the slot, the L-shaped profile and the positioning block disrupt the homogeneity of the material of the carrier at the position where the patient is located, so that there is a risk that the desired radiation dose into the tissue is not achieved.

Figure 4:
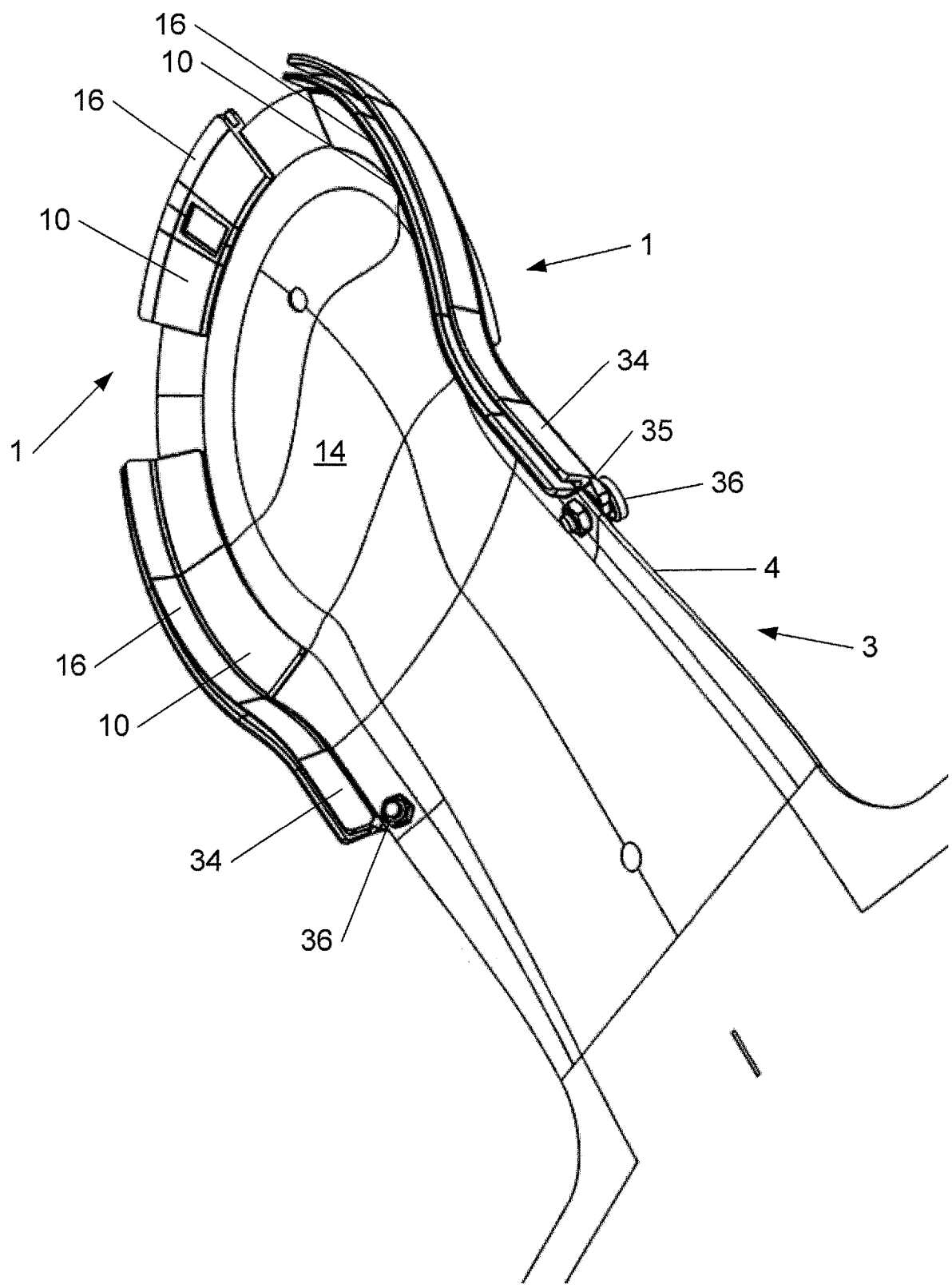
FIG. 4 shows a view to the upper side of a carrier.

A view to an upper side of a preferred embodiment of a carrier or base plate 3 for supporting a patient in radiation therapy is shown in FIG. 4. The preferred embodiment shown in FIG. 4 of the carrier 3 contains a top support surface 14 for supporting the patient. With "along" is meant that the connection means are located at a distance of the edge 4 of the carrier 3 or may be provided in one piece with the carrier, dependent on the nature of the connection means 21 on the profile. Along the edge of the carrier 3, preferably carrier connection means 13, as opposed to mask connection means 21, 22, comprising the first and the second connection means 21, 22, extend at least at one position, that are provided to cooperate with the mask connection means 21, 22 for the connection of the immobilization mask 2 with the carrier 3. Along the edge 4 of the carrier 3, there is provided preferably on at least one position, an opening 13 for receiving connection means 1 for attaching the immobilization mask 2 to the carrier 3. Along the edge 4 of the carrier 3, there is provided at least one swivel anchor point 36 for cooperation with swivel arm 34 extending along the connection means 1. More preferably, two or more openings 13 are provided. The number of openings 13 is usually chosen such that a sufficient amount of profiles 1 can be applied to enable a stable and accurate fixation of the position and posture of the body part of the patient and to allow not more than the desired range of motion. The openings 13 may be applied at random positions along the edge 4 of the carrier. However, preferably, the openings 13 are applied symmetrically relative to the longitudinal axis of the carrier to attain optimal distribution of the tension and tensile force over the immobilization mask 2 and to enable optimal derivation thereof to the carrier 3 (see FIG. 4). It is further possible to choose the number of openings 13 such that the carrier 3 is suitable for immobilizing multiple body parts with varying size. Every other arrangement of openings 13 considered suitable by the person skilled in the art may be chosen.

Furthermore, the carrier 3 along the edge 4 is preferably, at least on position 20, deformed for receiving a profile 1 for attaching the immobilization mask 2 to the carrier 3. The deformation 20 is preferably such that it is sufficiently large to receive the upper lip 10 of the profile 1 in such a way that the upper surface of the upper lip 10 is flush with the support surface 14 of the base plate or carrier 3 to increase the comfort of the patient. The presence of the deformation 20 hampers the displacement of the profile 1 along and relative to the edge of the carrier 4 and contributes in this way to the provision of a stable, accurate and reproducible connection to the immobilization mask 2 with the carrier. The deformation also counteracts the possibility of rotation of the profile 1 relative to the carrier 3. Preferably, two or more deformations 20 are provided. The number of deformations 20 is usually chosen such that a sufficient amount of profiles can be applied to enable a stable and accurate fixation of the position and posture of the body part of the patient and to allow no more than the desired range of motion. However, the presence of the deformation is not critical for the invention and can be omitted.

Figure 5:
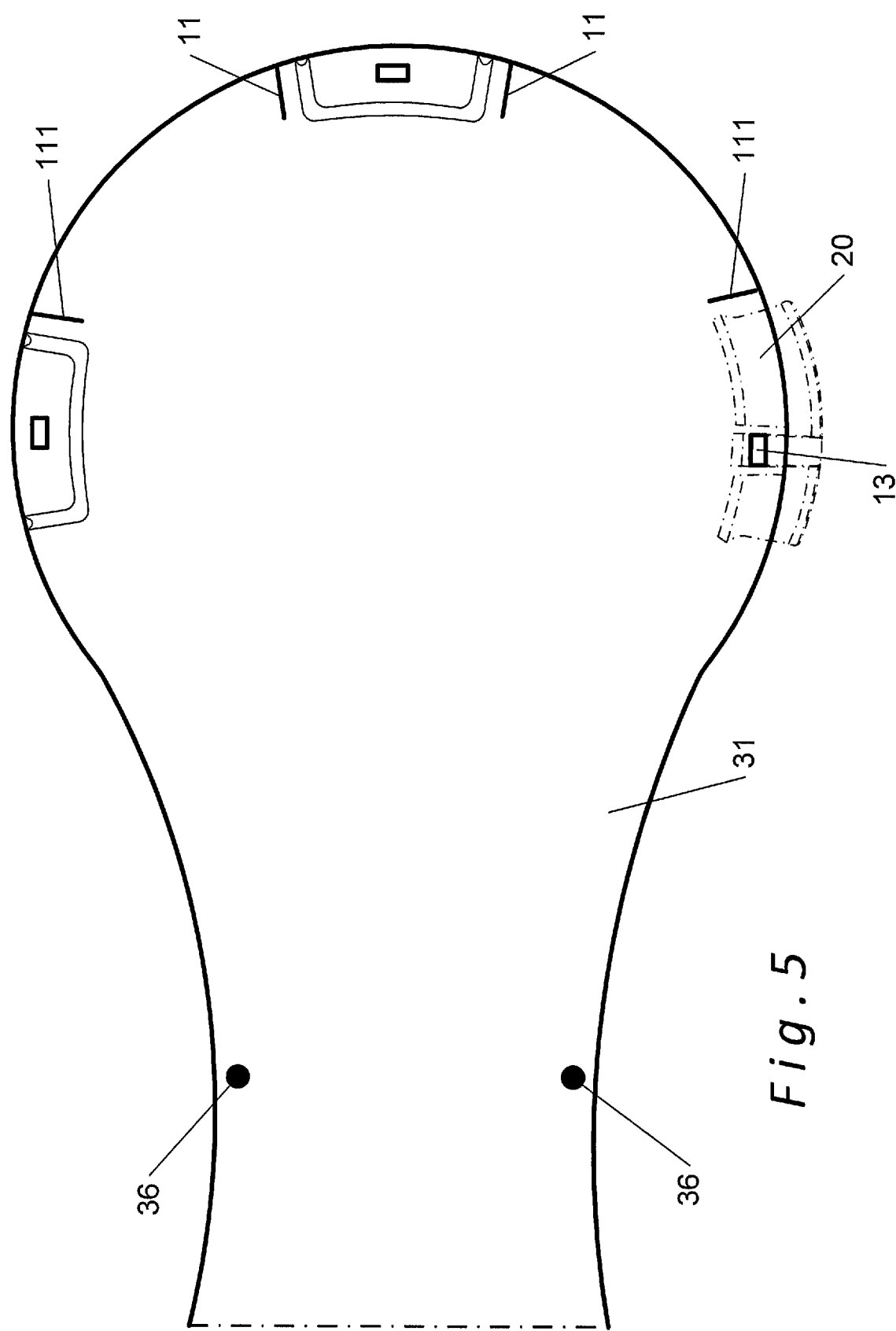
FIG. 5 shows a view to the lower side of a carrier.

The dimensions and shape of the deformations 20, if present, may be random. The deformation 20 preferably has the shape of a recess relative to the upper side of the carrier. In other words, the upper surface of the deformation 20 is preferably lowered relative to the upper surface 14 of the carrier. This is shown in FIG. 5. Preferably, the dimensions of the deformations 20 in the longitudinal direction along the edge 4 of the carrier and the dimensions of the deformation 20 in the traverse direction on the carrier 3 are aligned with the dimensions of the profile 1 or connection means that are provided to be incorporated into this deformation. The deformation 20 preferably has nearly the same dimensions as the profile 1 or is slightly larger than the profile 1, such that the profile 1 or at least the upper lip 10 of the profile can be incorporated in the deformation 20. The deformation 20 may function, at the application of the profile, as a guide for guiding the displacement of the profile 1 during the establishment of the connection between the mask 2 and the carrier 3. Since the raised edge of the deformation forms a barrier, the displacement of the profile 1, once installed, is opposed, and the deformation 20 contributes to the stable and accurate fixation of the position and posture of the body part of the patient so as to allow no more than the intended range of motion.

A view to the lower side of a preferred embodiment of a commonly used carrier 3 for supporting a patient, especially in proton therapy, is shown in FIG. 5. At a position between the edge 4 of the carrier and the opening 13, a guide 11, 111 is preferably provided at the lower side of the carrier for guiding the displacement of the profile 1 at the establishment of the connection of the immobilization mask 2 with the carrier 3, for example for guiding the displacement of the first lower lip 5 on the profile 1. A preferred embodiment of the guide 11 has for example the shape of two opposite protrusions 11 or rails, in between which, for example, the lip 5 of the profile 1 is displaceable at the establishment of the connection. The two opposite protrusions 11 can however also be positioned such that in between them, two opposing side edges of a profile can be slid, as for example shown in FIG. 5 for a profile not comprising a swivel arm and therefore not according to the invention. In such embodiment, the guide 11 for example has the shape of two opposite protrusions 11 or rails, in between which, for example, the second and the third lip 6, 7 are displaceable at the establishment of the connection. Otherwise, the guide 111 may also have the shape of a single protrusion provided to slide along an edge of the profile 1 according to the invention, preferably opposing the side of the profile from which the swivel arm 34 extends. Once the connection has been established, the protrusions counteract a displacement of the profile, for example the lip 5 and if present the second and the third lip 6, 7, in a direction along the edge and therefore contribute to a stable and accurate fixation of the position and posture of the body part of the patient. Instead of the protrusions or rails 11, an alternative guide, for example a slot or any other alternative deemed suitable by the person skilled in the art, may be used that is adapted to embodiment of the lower lip 5 and, if present, the second and the third lip 6, 7.

The connection means, more in particular the mask connection means of the connection means, preferably comprise a profile 1 with first connection means 21 at a first side of the profile along which the profile is connectable to the carrier 3, and second connection means 22 at a second side of the profile 1 opposite the first side along which the profile 1 is connectable to the immobilization mask 2. The first connection means 21 are provided, in the connected state, to engage an outer edge of the carrier. Such connection means enable to establish a connection between the immobilization mask 2 and the carrier 3, also when the profile is subjected to high tension. The first connection means 21 preferably engage in the thickness direction the outer edge of the carrier. In a possible embodiment, the first connection means 21 exercise a clamping force onto the carrier 3.

Figure 1:
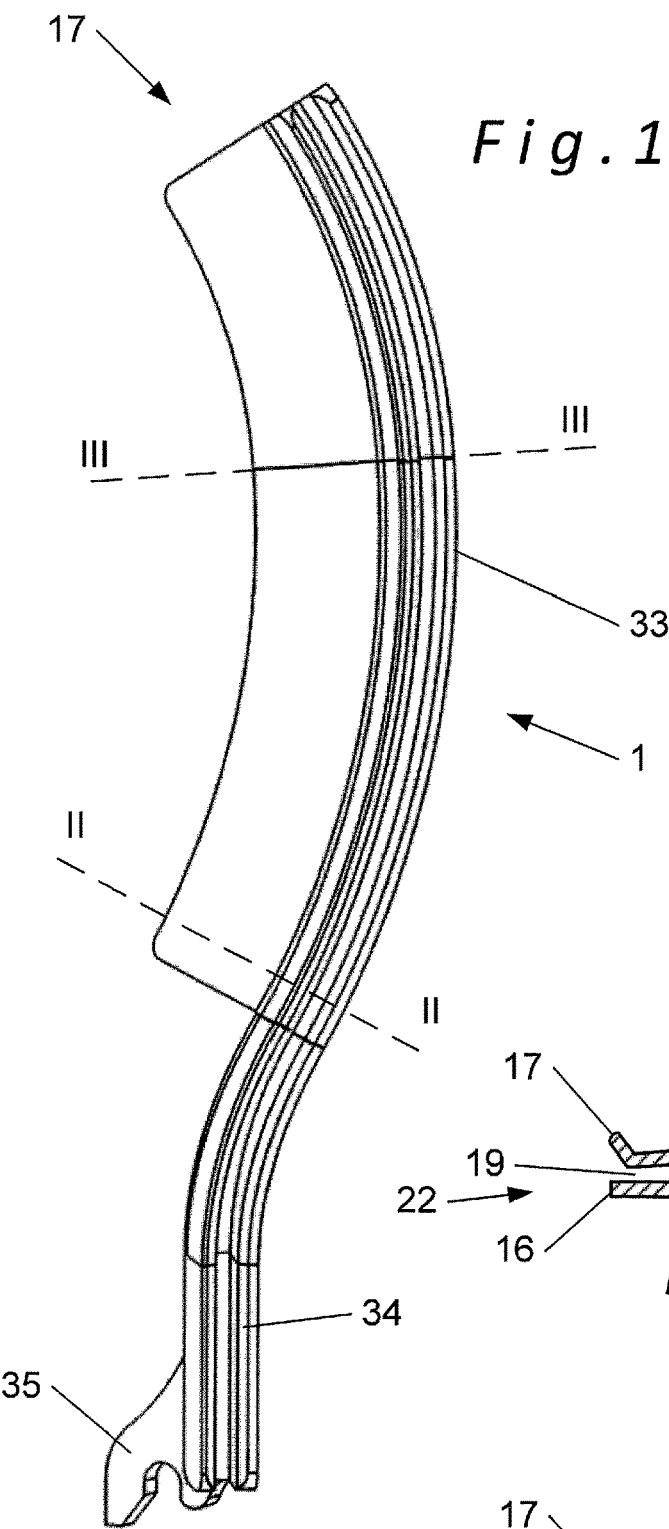
FIG. 1 shows a view of the lower side of the connection means (profile) for connecting an immobilization mask with the carrier for supporting a patient or a portion thereof.
Figure 2:
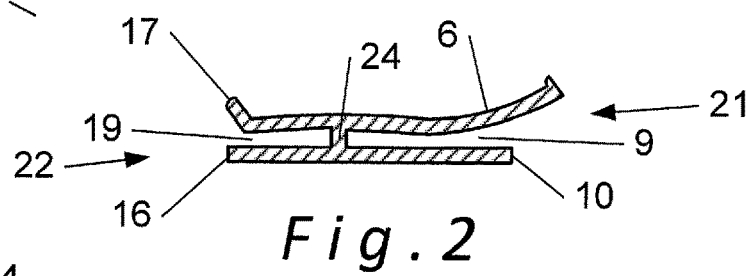
FIG. 2 shows a cross-section along the line II-II in FIG. 1.
Figure 3:
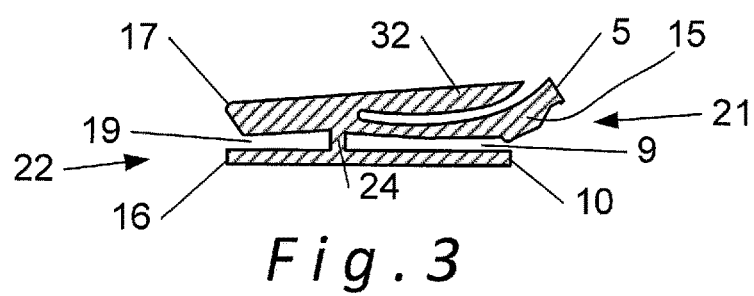
FIG. 3 shows a cross-section along the line III-Ill in FIG. 1.

The first connection means 21 preferably comprise an upper lip 10 that is provided to extend, in the connected state, along an upper surface or side of the carrier 14. Preferably, the upper lip 10 is incorporated in a corresponding deformation 20 along the upper surface 14 of the carrier 3. To enable a greater transmission of forces between the immobilization mask 2 and the carrier 3, the upper lip 10 preferably extends in the longitudinal direction along the edge 4 of the carrier 3. The upper lip 10 may, for example, be curved to optimally follow the shape of the immobilization mask 2, the upper lip 10 may however also be flat and rectangular or may take any other appropriate shape. The edge 33 of the upper lip may, for example, be curved to optimally follow the shape of the edge of the immobilization mask as shown in FIG. 1. The upper lip 10 increases the stability of the mask in the connected state with the carrier, since a tilting movement of the profile is counteracted.

The first connection means 21 preferably also comprise at least one lower lip 5 that is provided to extend in the connected state along a lower surface or lower side of the carrier 31. More preferably, the first connection means 21 comprise a lower lip 5 that is provided on the side directed to the carrier with a protrusion 15 that is provided, in the connected state, to engage corresponding connection means on the lower side of the carrier 3. Preferably, protrusion 15 engages a corresponding opening 13 in the carrier 3. The opening 13 may extend throughout the entire thickness of the carrier 3 or over a section thereof. The first connection means 21 further preferably comprise on a first side of the lower lip 5 a second lower lip 6 which preferably extends in the longitudinal direction along the edge of the carrier 3. The first connection means 21 further preferably comprise at a second side of the lower lip 5 opposite the first side in transverse direction of the lower lip 5, a third lower lip 7 which preferably extends in the longitudinal direction along the edge of the carrier 3. With a resiliently arranged lip 5, an easily detachable connection is provided between the profile 1, in particular between the profile and the carrier 3. The second and third lip 6, 7 may have the same or different shapes, but preferably have a corresponding shape. The second and third lower lips 6, 7 may, for example, be curved to optimally follow the shape of the immobilization mask, they may however also be rectangular or may take any other appropriate shape. The presence of the second and third lower lip 6, 7 increases the stability of the mask in the connected state with the carrier, since a tilting movement of the profile 1 is counteracted.

Preferably, at least one swivel arm 34 is provided extending along the connecting means 21, to connect with a corresponding swivel anchor point 36 located on the lower side of the carrier 31.

As can be seen in the figures, the swivel arm 34 and the swivel anchor point 36 can engage each other. In the embodiment shown in the figures, the engagement of the swivel arm 34 and the swivel anchor point 36 has substantially a single degree of freedom, in this case the angle of rotation of the swivel arm 34 around the swivel anchor point 36 during swivelling of the swivel arm 34. As can be seen in FIG. 1, the swivel arm 34 comprises a gripping part 35 provided to grip at least partly around the swivel anchor point 36. The gripping part 35 shown is in the form of a semi-circular shape provided to grip around a corresponding swivel anchor point 36. In the figures, the swivel gripping point 36 is in the form of a cylindrical protrusion provided to be surrounded at least partly by the gripping part 35 when it grips at least partly around the swivel anchor point 36. Such a connection can be provided in the form of a hinge joint allowing a single degree of freedom, in this case begin the angle of swivelling.

As can be seen in FIG. 1, the swivel arm extends along the first connection means 21 and the second connection means 22. Other embodiments are however possible, according to the desired configuration and depending on the specific use situation.

Figure 6:
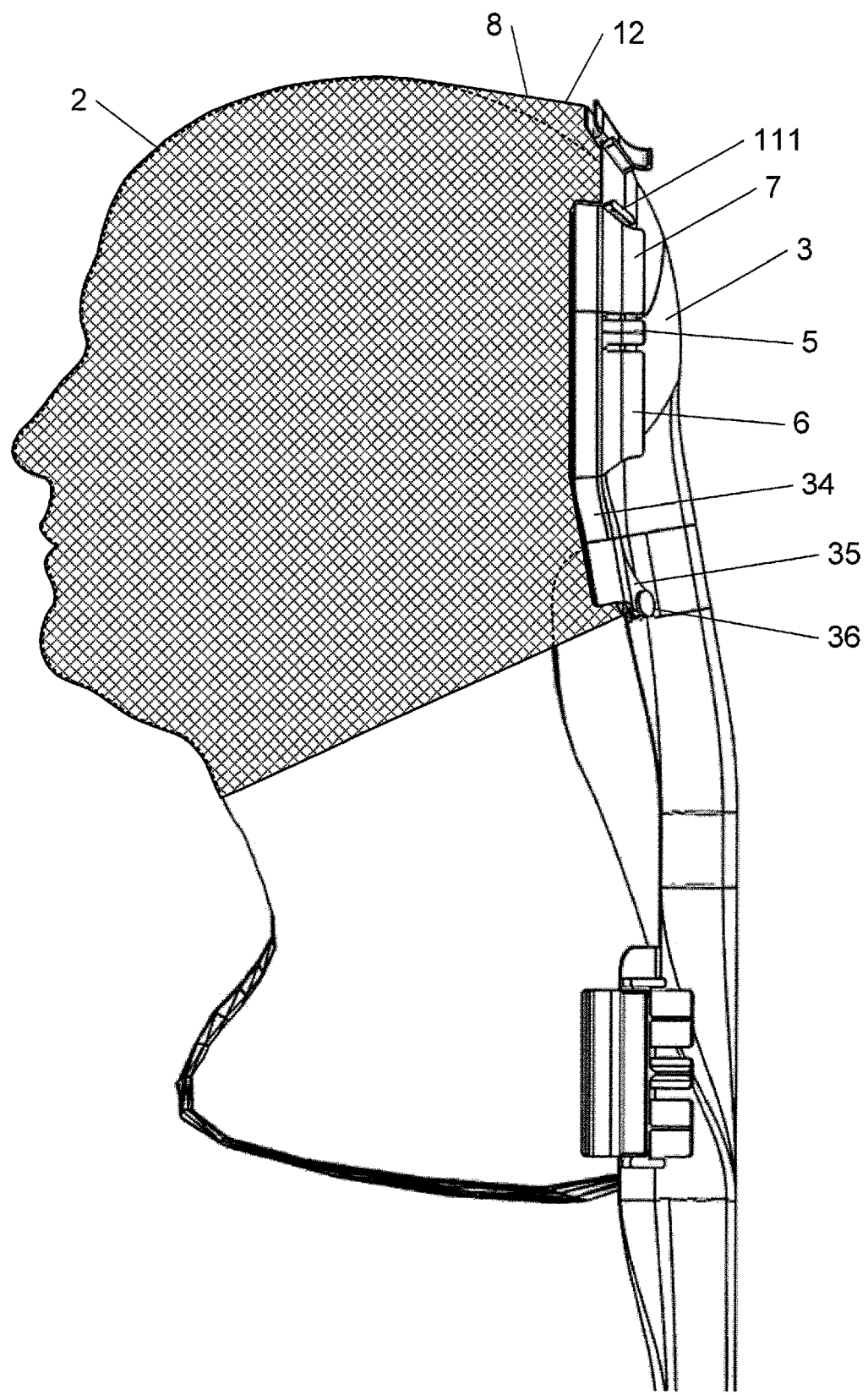
FIG. 6 shows an immobilization mask in the connected state with the carrier.

In FIG. 6 it can be seen that the body part to be immobilized is a head and the swivel anchor point 36 is provided below the mandible of the patient positioned on the carrier 3, more in particular, although not shown in FIG. 6, the swivel anchor point is provided below the mental protuberance of the mandible of the patient, even more in particular the swivel anchor point is provided at the height of the Adam's apple of the patient. It can further be seen that the body part is a head and the swivel anchor point 36 is located along the neck of a patient positioned on the carrier 3, more in particular above the clavicle of the patient.

FIG. 6 further shows the relative difficult position of the different connection means 21, 22 in light of attaching the connection means 21, 22 to the carrier 3.

Preferably, the outer surface of lip 5 further contains a second lip 32 that counteracts or even prevents a movement of the lip 5 that is directed away from the space 9. The presence of such lip however is not critical for the invention and the lip 32 can therefore be omitted.

The opening 13 can be arranged centrally in the deformation 20, if present, or asymmetrically.

The at least one upper lip 10 and at least one lower lip 5, 6, 7, of the first connection means 21 are preferably arranged at a distance from one another and are connected to each other at a connection position 24. Thereby, the first distance between the at least one upper lip 10 and at least one lower lip 5, 6, 7, is preferably chosen such that, at one first side of the connection position 24, it is sufficiently large for receiving a section of the carrier 3 that extends along the edge 4 thereof. The second connection means 22 preferably contain also an upper and a lower lip 16, 17 that are connected to each other at the connection portion 24. The upper and lower lip 16, 17 are preferably arranged at a second distance from each other that is sufficiently large for the inclusion of the material along the edge of the immobilization mask. The first distance can be equal to the second distance, or may be different from it. Connection portion 24 connects the first 21 and second connection means 22.

The first connection means 21 for connecting the profile to the carrier 3, preferably extends in a first direction relative to the connection portion 24, in particular in the direction of the carrier 3. The second connection means 22 that connect the profile 1 to the immobilization mask preferably extends in opposite direction relative to the first connection means 21 and the connection portion 24, in particular in the direction of the immobilization mask.

The carrier 3 may be provided in every material deemed suitable by the person skilled in the art. The carrier is for example conducted as a plate of carbon fibres impregnated with epoxy resin. However, other materials may be used.

The profile 1 may be provided in one piece with the immobilization mask 2 or as a separate component. Preferably, it is provided in one piece with the mask 2 in order to absorb higher tensile forces on the mask with minimal risk of releasing the profile 1. The profile 1 may be provided in another material than the mask, such that for both components the material may be chosen that is optimally adapted to the selected function it performs. This offers, for example, the possibility to choose the material for the mask such that it may directly be shaped to the patient, and to choose the material of the profile 1 such that it exhibits an optimal mechanical strength and minimal deformation to ensure an accurate and reproducible positioning.

Suitable materials for manufacturing the immobilization mask are for example thermoplastic elastomers, thermoplastic polyurethane, thermoplastic polyisoprene, thermoplastic polyesters, thermoplastic polyolefins, polyvinyl chloride, polystyrene, or a blend of two or more of these materials. Preferred are these polymers that have a relatively low softening temperature wherein the material is deformable, such that these are exceptionally suitable for the manufacturing of immobilization mask that can directly be formed onto the body part to be immobilized. The body part to be immobilized then serves as a mould for shaping the immobilization mask. Examples of suitable thermoplastic polyolefins comprise polyethylene, polypropylene or ethylene-propylene co-polymers. Examples of suitable thermoplastic polyesters comprise polyethylene vinyl acetate, polyacrylates or polymethacrylate, polymeric fatty acid esters, in particular poly-ϵ-caprolactone, for example poly-C-caprolactone such as available at Perstorp (UK) under the trade name Capa®. Preferred are the polymers of the group of thermoplastic polyurethane, isotactic polypropylene, copolymers of ethylene with 1-butene, a copolymer of ethylene with 1-octene, poly-ϵ-caprolactone, poly-ϵ-caprolactone containing thermoplastic polyurethane, as well as mixtures of two or more of these materials. Poly-ϵ-caprolactone is especially preferred because it has a low melting point and is deformable at temperatures that the human body can tolerate.

Suitable materials for manufacturing the profile are ABS, polyoxymethylene, polyamide or other equivalent materials.

This invention also concerns an immobilization mask for immobilizing a body part of the patient in a previously determined posture of the carrier 3, wherein the immobilization mask is provided with a profile 1 as described above, for connecting the mask 2 to the carrier 3 for supporting the patient. Preferably, the profile 1 is attached to the mask 2 along the edge of the mask 12, by incorporating the edge 12 of the mask in the second space 19 at the second connection means 22. Attachment can be done, for example, by gluing, by welding, by means of a mechanical connection or by any other connection deemed suitable by the person skilled in the art. Preferably, the connection is established by gluing or welding. Preferably, the profile 1 is as described above. To enable an optimal positioning and immobilizing along the edge of the mask, usually multiple profiles 1 will be applied.

This invention further concerns the profile 1 for connecting an immobilization mask 2 to the carrier 3, wherein the mask 2 is provided for immobilizing a body part of a patient in a predetermined posture on the carrier. Preferably, the profile 1 is as described above.

Connecting an immobilization mask 2 to the carrier 3 upon which a patient rests, for immobilizing for example the head of the patient occurs by covering the head of the patient with the immobilization mask that was shaped to the head of the patient. When use is made of an immobilization mask on which along the edge a plurality of profiles are attached, a connection is established by incorporating the edge 4 of the carrier 3 in the first space 9 of the profile 1 at the side of the first connection means 21, preferably at the height of a recess 20 in the carrier 3. When establishing the connection, the profile is usually placed transversal to the edge 4 of the carrier 3 in the direction of the middle of the carrier 3. The displacement of the profile 1 may be guided by the edges of the recess or deformation 20 at the upper side of the carrier 14 and by the guide 11 at the lower side 31 of the carrier that guides the displacement of the first lip 5 along the lower side 31 of the carrier 3 till the protrusion 15 engages the carrier at the first lip 5 in the corresponding opening 13.

LIST OF REFERENCE NUMBERS 1. profile
2. immobilization mask
3. carrier for patient
4. edge carrier for patient
5. first lower lip
6. second lower lip
7. third lower lip
8. sheet
9. first space
10. upper lip
11. guide
12. edge mask
13. carrier connection means
14. support surface carrier for patient
15. protrusion on first lower lip
16. upper lip second connection means
17. lower lip second connection means
18.
19. second space
20. deformation in carrier
21. first connection means
22. second connection means
23.
24. connection position
25. L-shaped profile
26. immobilization mask
27. carrier
28. slot in carrier
29. EVA block—
30.
31. lower side carrier
32. second lip
33. edge upper lip
34. swivel arm
35. gripping part
36. swivel anchor point
111. lateral guide

The invention claimed is:

1. A profile for connecting a carrier to an immobilization mask for immobilizing a body part of a patient on the carrier, the profile comprising:
a first connection means disposed at a second side of the profile for connecting the profile to the carrier,
a second connection means disposed at a first side of the profile opposite to the second side for connecting the profile to the immobilization mask, and
a swivel arm provided to cooperate with a swivel anchor point provided on the carrier, the swivel arm and the swivel anchor point being configured to cooperate such that when swivelling the swivel arm around the swivel anchor point towards the carrier, the first connection means are guided to a connected state in which the first connection means engages a corresponding connection means of the carrier.

2. The profile according to claim 1, wherein the first connection means comprise an upper lip that is configured, in the connected state, to extend along an upper surface of an edge of the carrier, and a first lower lip that is configured, in the connected state to extend along a lower side of the carrier and to engage the corresponding third carrier connection means at the lower side of the carrier.

3. The profile according to claim 2, wherein the lower lip is arranged resiliently.

4. The profile according to claim 2, wherein the first lower lip on a side directed to the carrier is provided with a protrusion that is configured, in the connected state, to engage the corresponding third carrier connection means at the lower side of the carrier.

5. The profile according to claim 2, wherein the first connection means further comprise a second lower lip and a third lower lip at opposite sides of the first lower lip, wherein the second lower lip and the third lower lip extend along the lower side of the carrier.

6. The profile according to claim 1, wherein the swivel arm and the swivel anchor point engage each other.

7. The profile according to claim 6, wherein the engagement of the swivel arm and the swivel anchor point has substantially a single degree of freedom.

8. The profile according to claim 7, wherein the angle of rotation of the swivel arm around the swivel anchor point during swivelling of the swivel arm is the substantially single degree of freedom.

9. The profile according to claim 1, wherein the swivel arm comprises a gripping part configured to grip at least partly around the swivel anchor point.

10. The profile according to claim 9, wherein the swivel anchor point comprises a cylindrical protrusion configured to be surrounded at least partly by the gripping part when it grips at least partly around the swivel anchor point.

11. The profile according to claim 1, wherein the swivel arm and the swivel anchor point are connected to each other in a hinge joint.

12. The profile according to claim 1, wherein the first connection means on the profile comprises mask connection means that are complementary to and are provided to cooperate with the corresponding third carrier connection means, and whereby the corresponding third carrier connection means are positioned along an outer edge of the carrier.

13. The profile according to claim 1, wherein the swivel arm extends along the first connection means.

14. The profile according to claim 1, wherein the swivel arm extends along the second connection means.

15. An immobilization mask for immobilizing a body part of a patient on a carrier, the immobilization mask comprising a sheet of a thermoplastic material for receiving the body part to be immobilized, and at least one profile for connecting the immobilization mask to the carrier according to claim 1, wherein the profile is connected to the sheet of thermoplastic material at the first side of the at least one profile comprising the second connection means.

16. The immobilization mask according to claim 15, wherein the sheet of thermoplastic material for receiving the body part to be immobilized is chosen from the group, consisting of thermoplastic elastomers, thermoplastic polyurethane, thermoplastic polyisoprene, thermoplastic polyesters, thermoplastic polyolefins, polyvinyl chloride, polystyrene, or a blend of two or more of these materials.

17. The immobilization mask according to claim 15, wherein the sheet of thermoplastic material is covered with an antibacterial coating.

18. An assembly for radiation therapy comprising a carrier for supporting a patient, and an immobilization mask according to claim 15 connectable with the carrier for immobilizing a body part of the patient onto the carrier.

19. A method for immobilizing a body part of a patient on a carrier using an immobilization mask, the method comprising the step of providing the immobilization mask is in accordance with claim 15, the method further comprising the step of immobilizing a body part of a patient on a carrier using the immobilization mask.

20. The method in accordance with claim 19, wherein the method further comprises the step of immobilizing the body part of the patient during radiation therapy.

* * * * *